United States Patent
Schmitt et al.

[11] Patent Number: 6,138,315
[45] Date of Patent: Oct. 31, 2000

[54] ANTIMICROBIAL ACTIVE COMPOUNDS

[75] Inventors: William Howard Schmitt, Branford; Robert Alfread Bennett, Easton; Richard Steven Hart, Naugatuck, all of Conn.

[73] Assignee: Chesebrough-Pond's USA Co., Divison of Conopco, Inc., Greenwich, Conn.

[21] Appl. No.: 09/006,554

[22] Filed: Jan. 13, 1998

[51] Int. Cl.⁷ ........................................ A46B 9/04
[52] U.S. Cl. .......................... 15/167.1; 15/207.2; 422/1
[58] Field of Search ................ 15/207.2, 167.1; 422/1, 40, 28; 252/389.23; 424/54, 49

[56] References Cited

U.S. PATENT DOCUMENTS

| | | |
|---|---|---|
| 2,919,200 | 12/1959 | Dubin et al. . |
| 3,302,230 | 2/1967 | Poppelman . |
| 3,589,823 | 6/1971 | Hendrickson ............... 15/167.1 |
| 3,691,585 | 9/1972 | Flom ....................... 15/104.94 |
| 4,152,804 | 5/1979 | Morris ..................... 15/104.94 |
| 5,015,504 | 5/1991 | Gent et al. ................. 427/284 |
| 5,300,290 | 4/1994 | Spencer .................... 15/167.1 |
| 5,310,563 | 5/1994 | Curtis et al. ............... 424/616 |
| 5,474,739 | 12/1995 | Triestram et al. ........... 422/40 |

FOREIGN PATENT DOCUMENTS

| | | |
|---|---|---|
| 406154030 | 6/1994 | Japan . |
| WO98/51189 | 11/1998 | WIPO . |

OTHER PUBLICATIONS

Reach® Antimicrobial Toothbrush with Microban® Advertisement—1997.

*Primary Examiner*—Krisanne Thornton
*Attorney, Agent, or Firm*—Milton L. Honig

[57] ABSTRACT

A unitarily constructed toothbrush is provided including a head with bristles unitarily molded therewith, a handle and a neck, all being formed of an identical plastic material. Dispersed throughout the plastic material is at least one anti-microbial active compound such as a halogenated hydrocarbon, a quaternary ammonium salt or combinations thereof. Preferably the plastic material is a low density polyethylene. Toothbrushes of the present invention inhibit the growth of bacteria and other micro-organisms thereby avoiding the possibility of infecting oral gums.

7 Claims, 1 Drawing Sheet

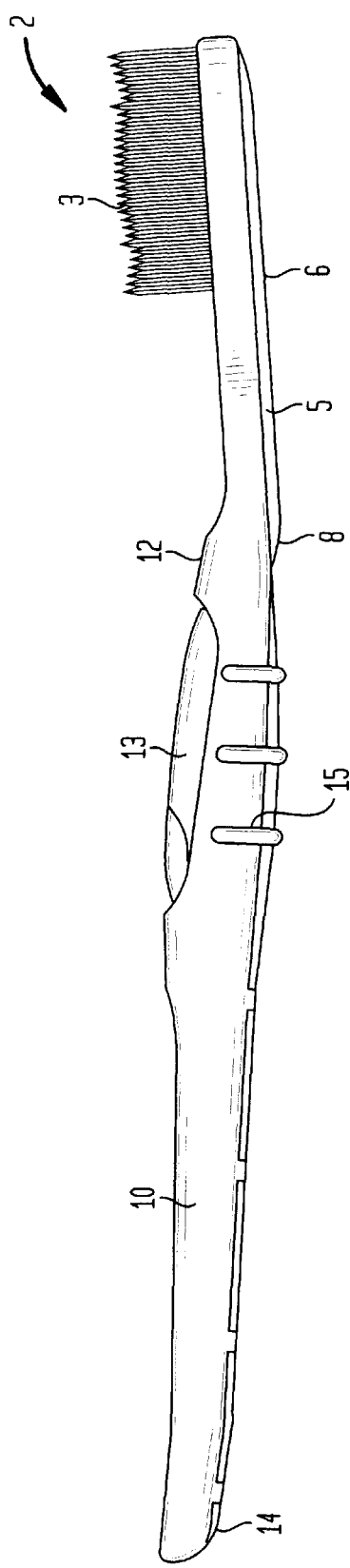

6,138,315

ANTIMICROBIAL ACTIVE COMPOUNDS

BACKGROUND OF THE INVENTION

1. Field of the Invention

The invention concerns a toothbrush incorporating anti-microbial active compounds.

2. The Related Art

Toothbrush surfaces are magnets for bacteria. Surfaces are often wet which encourages transfer. Moreover, the human oral cavity is a rich source of microbial life which can attach to wetted surfaces.

Serious medical problems can arise from microbial contamination. For instance, after periodontal surgery, a patient is quite vulnerable to infection. Deep gum pockets result from the treatment which expose roots of the tooth. These root areas must be kept clean.

Re-transfer of oral originating microbes is not the only concern. Airborne bacteria of many varieties are especially prevalent in bathrooms. These nonoral organisms can attach to wet toothbrushes and thereby eventually travel into the mouth. Risks of microbial contamination are therefore great. The problem has been recognized and attempts have been reported to find solutions.

Toothbrushes are generally constructed from one or more plastic materials forming a handle. Polypropylene is one of the most popular handle material. Moderately high temperatures are needed to process polypropylene through injection molding apparatus. Unfortunately most of the effective and suitable anti-microbial agents, such as triclosan, begin to degrade at about 150° C. Decomposition is less of a problem with handles produced through cast molding techniques. Of course, resins suitable for casting such as polymethylmethacrylate are more expensive than polypropylene.

An even greater issue is treatment of the bristles. These invariably are nylon filaments. Extremely high temperatures of over 200° C. are necessary in the extrusion of nylon filament. Quite clearly temperature sensitive actives cannot be dispersed within the nylon during the extrusion process.

Microban® Products Company in conjunction with Johnson & Johnson have launched an anti-microbial version of the Reach® toothbrush. Thermal degradation problems have been minimized by first incorporating the anti-microbial active into a bead of polymer by low temperature extrusion. The beads are then re-heated at higher temperatures through an injection die that molds toothbrush handles. Unfortunately, bacteria can also contaminate the handles, especially the tuft holes in which the handles are inserted. Therefore, it would be desirable to obtain anti-microbial protection for all surfaces of a toothbrush.

Accordingly, it is an object of the present invention to provide a toothbrush with both bristles and handle incorporating anti-microbial active compounds.

Another object of the present invention is to provide a toothbrush which can be manufactured at relatively low cost yet includes the benefit of anti-microbial protection on all surfaces of the toothbrush.

Still another object of the present invention is to provide a toothbrush which provides a broad spectrum of anti-microbial activity.

These and other objects of the present invention will become more readily apparent through the following summary and detailed discussion.

SUMMARY OF THE INVENTION

A unitarily constructed toothbrush is provided including:
a head with bristles unitarily formed with the head;
a neck with first and second ends, the first end connected to the head; and
a handle with front and rear ends, the front end connected to the second end of the neck, wherein the head with bristles, neck and handle are all formed of an identical plastic material, the material including dispersed therein at least one anti-microbial active compound.

BRIEF DESCRIPTION OF THE DRAWINGS

The above features, advantages and objects of the present invention will more fully be appreciated through the following detailed discussion, reference being made to the drawing having a sole FIGURE.

DETAILED DESCRIPTION OF THE INVENTION

Toothbrushes according to the present invention may have a wide variety of shapes and designs. The FIGURE illustrates only one of a multitude of designs. The toothbrush is characterized by a head 2 having bristles 3, a neck 5 with first and second ends 6, 8 and a handle 10 with front and rear ends 10, 14. An ornamental faux pad 13 and rings 15 are shown in the preferred embodiment, but need not be present for purposes of this invention.

All parts of toothbrushes according to the invention are unitarily constructed together from an identical plastic material. The most preferred plastic material is polyolefin such as low density polyethylene. Advantageously the plastic material will have a Melt Index greater than 5, preferably from 6 to 30, optimally from 10 to 25 g/10 min.

Ordinarily the toothbrushes are formed by injection molding through a conventional plastic injection molding machine which molds the head, neck and handle together in a single shot. A hopper with starting pellets is conventionally utilized to feed materials to an extruder and then to an injection molding die. Pellets of plastic and of solid anti-microbial active compound are fed to the hopper. Where the active is liquid at room temperature, the anti-microbial may be introduced by liquid injection. Processing temperatures within the extruder portion of the molding machine are maintained in a range of 50° C. to 220° C., preferably in the range 65° C. to 200° C.

A wide variety of anti-microbial active compounds may be employed. These actives may generally be classified as halogenated hydrocarbons, quaternary ammonium salts and sulfur compounds. Halogenated hydrocarbons include halogenated derivatives of salicylanilides, carbanilides, bisphenols, diphenyl ethers, anilides of thiophene carboxylic acids and chlorhexidines. Quaternary ammonium compounds include alkyl ammonium, pyridinum, and isoquinolinium salts. Sulfur active compounds include thiuram sulfides and dithiocarbamates.

Among the halogenated salicylanilides there may be mentioned the following derivatives:

5-bromo-salicylanilide
4',5-dibromo-salicylanilide
3,4',5-tribromo-salicylanilide
6-chloro-salicylanilide
4'5-dichloro-salicylanilide
3,4'5-trichloro-salicylanilide
4',5-diiodo-salicylanilide
3,4',5-triiodo-salicylanilide
5-chloro-3'-trifluoromethyl-salicylanilide
5-chloro-2'-trifluoromethyl-salicylanilide 3,5-dibromo-3'-trifluoromethyl-salicylanilide
3-chloro-4-bromo-4'-trifluoromethyl-salicylanilide
2',5-dichloro-3-phenyl-salicylanilide
3',5-dichloro-4'-methyl-3-phenyl-salicylanilide
3',5-dichloro-4'-phenyl-3-phenyl-salicylanilide
3,3',5-trichloro-6'-(p-chlorophenoxy)-salicylanilide
3',5-dichloro-5'-(p-bromophenoxy)-salicylanilide
3,5-dichloro-6'-phenoxy-salicylanilide
3,5-dichloro-6'-(o-chlorophenoxy)-salicylanilide
5-chloro-6'-(o-chlorophenoxy)-salicylanilide
5-chloro-6'-beta-naphthyloxy-salicylanilide
5-chloro-6'-alpha-naphthyloxy-salicylanilide
3,3',4-trichloro-5,6'-beta-naphthyloxy-salicylalide;

Halogenated carbanilides are represented by the 3,4,4'-trichloro-carbanilide and the 3,3',4-trichloro derivatives and by 3-trifluoromethyl-4,4'-dichlorocarbanilide.

The bis-phenols are represented by the following:
2,2'-methylenebis(4-chlorophenol)
2,2'-methylenebis(4,5-dichlorophenol)
2,2'-methylenebis(3,4,6-trichlorophenol)
2,2'-thiobis(4,6-dichlorophenol)
2,2'-diketobis(4-bromophenol)
2,2'-methylenebis(4-chloro-6-isopropylphenol)
2,2'-isopropylidenebis(6-sec-butyl-4-chlorophenol)

Examples of quaternary ammonium compounds are:
Cetyl pyridinium chloride
Diisobutylphenoxyethoxyethyldimethylbenzylammonium chloride
N-methyl-N-(2-hydroxyethyl)-N-(2-hydroxydodecyl)-N-benzyl ammonium chloride
Cetyl trimethylammonium bromide
Stearyl trimethylammonium bromide
Oleyl dimethylethylammonium bromide
Lauryldimethylchlorethoxyethylammonium chloride
lauryldimethylbenzylammonium chloride
Alkyl ($C_8$–$C_{18}$)dimethyl(3,4-dichlorobenzyl)-ammonium chloride
Lauryl pyridinium bromide
Lauryl isoquinolinium bromide
N(lauroyloxyethylaminoformylmethyl)pyridinium chloride;

Examples of the thiocarbamates and the thiuram sulfides are:
disodium ethylene bis-dithiocarbamate (Nabam)
diammonium ethylene bis-dithiocarbamate (amabam)
Zn ethylene bis-dithiocarbamate (ziram)
Fe ethylene bis-dithiocarbamate (ferbam)
Mn ethylene bis-dithiocarbamate (manzate)
tetramrethyl thiuram disulfide
tetrabenzyl thiuram disulfide
tetraethyl thiuram disulfide
tetramethyl thiuram sulfide From the viewpoint of safety and effectiveness the preferred antibacterial agents are as follows:
4',5-dibromosalicylanilide
3,4',5-tribromosalicylanilide
3,4',5-trichlorosalicylanilide
3,4,4'-trichlorocarbanilide
3-trifluoromethyl4,4'-dichlorocarbanilide
2,2'-methylenebis(3,4,6-trichlorophenol)
2,4,4'-trichloro-2'-hydroxydiphenyl ether
Tyrothricin
N-methyl-N-(2-hydroxyethyl-N-(2-hydroxydodecyl)-N-benzylammonium chloride
Cetyl pyridinium chloride Especially preferred are:
2,3'5-tribromosalicylanilide
chlorohexidine digluconate
chlorohexidine diaceate
4',5-dibromosalicylanilide
3,4,4'-trichlorocarbanilide
2,4,4'-trichloro-2-hydroxydiphenyl ether
Cetyl pyridinium chloride Most preferred among the halogenated hydrocarbons is 2,4,4'-trichloro-2-hydroxydiphenyl ether (known generically as) TRICLOSAN and among the quaternary ammonium salts is cetyl pyridinium chloride. Indeed, combinations of both of these active substances allow for a broad range of anti-microbial activity in the toothbrushes of the present invention.

The following example will more fully illustrate the embodiments of this invention. All parts, percentages and proportions referred to herein and in the appended claims are by weight unless otherwise indicated.

EXAMPLE

Anti-microbial efficacy of toothbrushes according to the present invention was evaluated in the manner described below.

Test microorganisms and media were prepared in the following manner. One tube of FDA broth culture was inoculated with a microorganism and incubated at 37° C. for 20–24 hours. Microorganisms suitable for this type culture were *S. aureus, S. epidermidis, K. pneumoniae, E. coli, P. aeruginosa*, and *S. mutans*. From the 20–24 hour culture is taken 1 ml of a 1:100 dilution in saline which is added to a 200 ml of melted Extract-FDA agar previously cooled to approximately 45° C.

To each of 3 plates per sample, plus one control plate, there is added 15 ml of agar. The agar is allowed to solidify. Six ml of innoculated agar is added to the solid sterile agar surface and spread evenly across the plate. It is allowed to solidify. The toothbrush is then placed on the innoculated agar surface. It is pressed slightly to make good surface contact. The petri dishes are then fitted with either unglazed porcelain covers or covers lined with sterile filter paper. Plates are incubated in an upright position for 24 hours at 37° C.

Zones of inhibition are now determined. These are measured with a Fisher Lilly Antibiotic Zone Reader with a scale in millimeters. At least 3 measurements are performed per plate to establish distance from the edge of each petri dish to the closest microbial growth. An average of the 3 measurements are taken and reported as the Average Zone of Inhibition.

TRICLOSAN was incorporated through co-extrusion and injection molding with low density polyethylene into a toothbrush with unitarily formed handle, neck and head/bristles. Various levels of TRICLOSAN were evaluated. Cetyl pyridinium chloride was investigated as an alternative anti-microbial agent in the aforedescribed toothbrushes. Table I lists the zone of inhibition results.

TABLE I

| | | ZONE SIZE (mm) | | | | | |
|---|---|---|---|---|---|---|---|
| ANTI-MICROBIAL ACTIVE | PERCENT ACTIVE | P. AERUGINOSA | K. PNEUMONIAE | S. AUREUS | E. COLI | S. EPIDERMIDIS | S. MUTANS |
| Triclosan | 2.0 | 0 | 10.6 | 10.3 | 3.6 | 10.2 | 0 |
| Triclosan | 1.0 | 0 | 9.5 | 12.2 | 7.0 | 10.4 | 0 |
| Triclosan | 0.5 | 0 | 6.6 | 12.5 | 0.8 | 8.6 | 0 |
| Triclosan | 0.25 | — | 2.6 | 3.6 | 0 | 5.8 | — |
| Cetyl Pyridinium Chloride | 0.2 | 0 | 1.3 | 2.8 | 0 | 5.2 | 2.4 |

The foregoing description and examples illustrate selected embodiments of the present invention. In light thereof variations and modifications will be suggested to one skilled in the art, all of which are within the spirit and purview of this invention.

What is claimed is:

1. A unitarily constructed toothbrush comprising:
   a head with bristles unitarily formed with the head;
   a neck with first and second ends, the first end connected to the head; and
   a handle with front and rear ends, the front end connected to the second end of the neck, wherein the head with bristles, neck and handle are all formed of an identical plastic material, the material including dispersed therein at least one anti-microbial active compound.

2. The toothbrush according to claim 1 wherein the plastic material is a low density polyethylene.

3. The toothbrush according to claim 1 wherein the anti-microbial active compound is a halogenated hydrocarbon.

4. The toothbrush according to claim 3 wherein the halogenated hydrocarbon is 2,4,4'-trichloro-2-hydroxydiphenyl ether.

5. The toothbrush according to claim 3 further comprising a second anti-microbial active compound which is a quaternary ammonium salt.

6. The toothbrush according to claim 5 wherein the quaternary ammonium salt is a $C_1$–$C_{22}$ pyridinium salt.

7. The toothbrush according to claim 6 wherein the pyridinium salt is cetyl pyridinium chloride.

* * * * *